United States Patent [19]
Barker

[11] Patent Number: 4,891,993
[45] Date of Patent: Jan. 9, 1990

[54] APPARATUS AND METHOD FOR MEASUREMENT OF URINE VOID VOLUMES

[75] Inventor: Kent R. Barker, Eagan, Minn.

[73] Assignee: Prevention Sciences Incorporated, Eagan, Minn.

[21] Appl. No.: 252,456

[22] Filed: Sep. 30, 1988

[51] Int. Cl.[4] .............................................. G01N 1/14
[52] U.S. Cl. ............................. 73/863.52; 73/863.02; 73/861.08
[58] Field of Search ............... 73/863.01, 863.52, 223, 73/294, 304 R, 861, 861.08; 128/766, 771; 340/603, 606, 608, 618, 620; 324/442

[56] References Cited

U.S. PATENT DOCUMENTS

| | | | |
|---|---|---|---|
| 2,626,385 | 1/1953 | Schumann | 340/239 |
| 2,859,956 | 11/1958 | Meriam | 265/8 |
| 3,389,601 | 6/1968 | Semplak | 73/171 |
| 3,493,951 | 2/1970 | Hartka et al. | 73/861.08 |
| 3,701,713 | 10/1973 | Eaton et al. | 324/442 |
| 3,754,220 | 8/1973 | Sztamler et al. | 340/239 |
| 3,930,411 | 1/1976 | Beeker et al. | 73/223 |
| 4,051,431 | 9/1977 | Wurster | 324/61 R |
| 4,144,751 | 3/1979 | Yokoyama | 73/194 |
| 4,343,316 | 8/1982 | Jespersen | 128/771 |
| 4,395,918 | 8/1983 | Wilson | 73/861 |
| 4,473,530 | 9/1984 | Villa-Real | 73/863.52 |
| 4,484,582 | 11/1984 | Rottenberg et al. | 73/861.08 |
| 4,488,438 | 12/1984 | Tomita | 73/861 |
| 4,519,248 | 5/1985 | Torii et al. | 73/863.52 |
| 4,532,936 | 8/1965 | Le Veen et al. | 128/771 |
| 4,559,831 | 12/1985 | Prestele | 73/861.08 |
| 4,672,856 | 6/1987 | Marrs et al. | 73/863.52 |
| 4,683,435 | 7/1987 | Blades | 324/442 |
| 4,701,713 | 10/1987 | Eaton el al. | 324/442 |

OTHER PUBLICATIONS

Article for Osamu Tochikubo, M.D. et al entitled "Simple Portable Device for Sampling a Whole Day's Urine and its Application to Hypertensive Outpatients", dated Mar. 29, 1982, publication date not known.

*Primary Examiner*—Robert R. Raevis
*Attorney, Agent, or Firm*—Kinney & Lange

[57] ABSTRACT

An apparatus and method for electronic measurement of urine volumes. The invention provides a device for establishing streams of uniform flow from a urine void by a user. The urine streams are passed by electrodes whereby resistivity changes in a current path between the electrodes indicates beginning and cessation of urine flow. Timing of the duration of the streams provides a measurement of urine volume per void.

11 Claims, 2 Drawing Sheets

APPARATUS AND METHOD FOR MEASUREMENT OF URINE VOID VOLUMES

BACKGROUND OF THE INVENTION

1. Field of the Invention

The present invention relates to an apparatus and method for measuring void instance volumes of urine generated by an individual.

2. Technical Background of the Invention

Urine collection and analysis is an effective and potentially highly accurate indirect approach to measurement of dietary sodium intake by an individual. Over the long term, all sodium which is absorbed by the body from the gastro-intestinal track must leave it again, and virtually all of the absorbed sodium which leaves the body leaves it through urine. Where an individual remains at approximately the same weight over a sufficiently longer period of time, the amount of sodium leaving the individual's body through urine accurately reflects the amount of sodium absorbed from the individual's diet.

Physicians are interested in dietary sodium because of a believed link between high rates of dietary sodium intake and incidence of elevated blood pressure (hypertension). While the existence of such a relationship is controversial, availability of improved data, tracking dietary sodium intake and blood pressure, would provide improved circumstantial evidence regarding the existence of such a link. In addition, the availability of such data would allow a doctor to judge the effectiveness of a low sodium diet on an individual's blood pressure and an individual's adherence to a prescribed low sodium diet.

Up to the present, efforts to generate data regarding dietary sodium intake have frequently proven expensive, and nearly always inconvenient. Direct techniques of measuring sodium intake have included such methods as, for example, preparation of duplicate meals, one to be consumed and the second to be burned to recover the sodium for measurement. Another technique has been to prepare meals with essentially no sodium content, and to thereafter add measured amounts of sodium containing compounds. Such experiments are tedious and expensive, and bear little relationship with actual day to day life in the case of an individual undergoing treatment for blood pressure.

Because of the difficulties attendant to direct measurement of sodium intake, interest in indirect methods has increased. Sodium levels and quantities excreted in urine provide a superior method of determining dietary sodium intake. Current practice requires collection of urine in bottles. An individual collects urine for 24 hours and brings the sample to a laboratory for analysis. At the laboratory, the volume and sodium concentration are measured and multiplied to find the total quantity of sodium excreted. The procedure is repeated over a period of days.

It is evident that only the strong of will will be inclined to carry a jug containing up to 2 liters of urine, remembering to void only into the jug during the course of the day. Difficulties in maintaining such a regimen have resulted in weekday urine collection often not adequately representing sodium intake.

SUMMARY OF THE INVENTION

The invention provides for urine volume measurement using a portable apparatus providing for the measurement of urine volume per void, retention of data representing the measurement and when taken, and allowing retention of a sample of each void, identified by the time taken. The retained samples represent only a fraction of the total urine produced, thus eliminating the problems caused by carrying about a bulky container. The retained samples can be delivered to a laboratory for analysis of the sodium levels of each sample and correlation with the volume data associated with each respective void instance. This allows calculation of the quantity of sodium excreted. Advantageously, such analyses indicate the rate of sodium excretion and volume rates of urine production through the day.

The portable apparatus provides urine volume measurement through a flow rate leveling funnel. Electrodes are disposed opposite one another on the inside of a funnel drainage tube. When the tube is dry, no current is conducted between the electrodes. Urine is electrically conductive, although its conductivity varies as a function of sodium ion concentration, and accordingly, when urine is flowing through the funnel drainage tube a conductive path exists between the electrodes.

An alternating voltage, preferably with a square wave function, is applied to one of the electrodes during use. An alternating signal through the urine avoids substantial electrolysis of the urine, and the consequent effect electrolysis would have on conductivity of the urine. The opposite electrode reflects the square wave with the voltage attenuated as a function of conductivity of the urine. After the flow of urine stops, a film of urine generally will coat the inside of the funnel drainage tube, providing a conductive path of greatly reduced conductivity between the electrodes which decreases thereafter with time. Experiment has determined that the conductivity of this path is initially a substantially constant proportion of the conductivity of the preceding urine flow.

A circuit is provided for generating a DC output as a logarithm of the absolute magnitude of the signal appearing on the second electrode. The slope of the DC output signal during periods when urine flow is beginning or ending will be of the same time rate of change, but of opposite polarity, each occurrence. The time derivative of the output of the logarithm circuit comprises substantially identical magnitude, opposite polarity pulses indicating the beginning and the ending of flow through the funnel. Because flow is constant, a timer can be used triggered by the beginning and cessation of flow to determine the quantity of flow. A sample of the urine flow instance is taken and located in a vial, on which the patient records the time and volume of the measurement.

The apparatus of the present invention is portable and unitary, easily handled, cleaned after use and stored when not in use to make urine measurement easy and simple for the patient.

DETAILED DESCRIPTION OF THE PREFERRED EMBODIMENT

Figure 1:
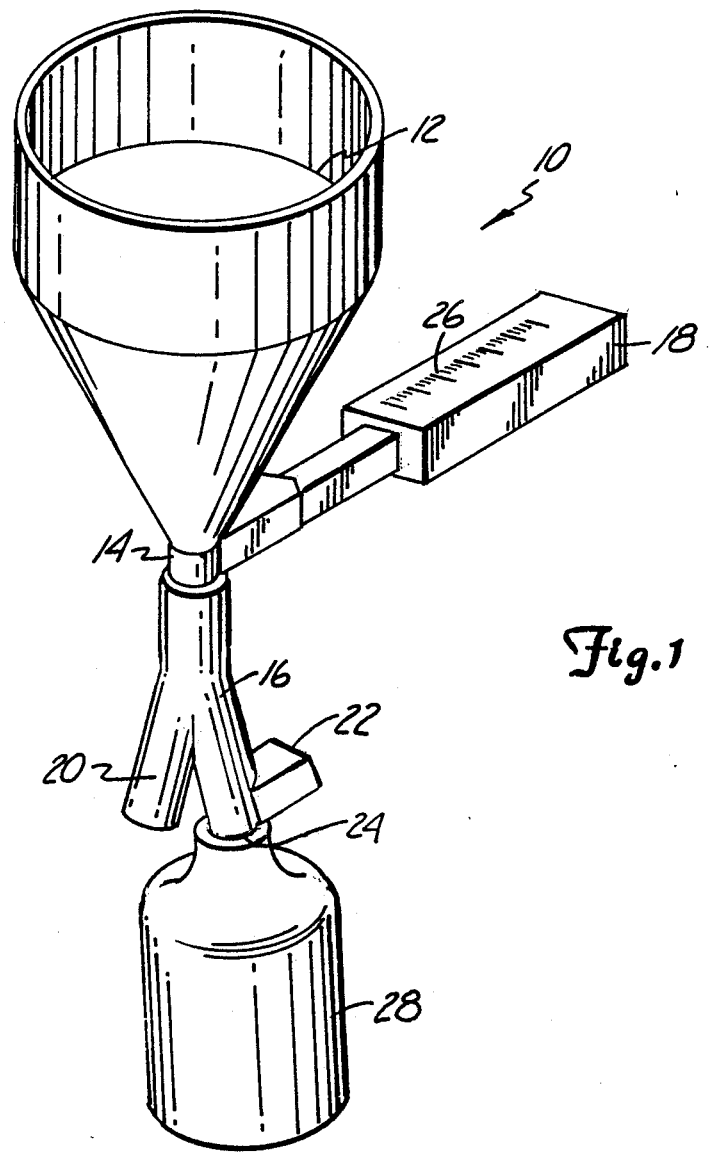
FIG. 1 is a perspective view of the urine volume measuring apparatus and samping tube of the present invention.

FIG. 1 illustrates a hand held urine volume measuring instrument 10. Measuring instrument 10 includes a flow leveling funnel 12 for the user to urinate into, an outflow conduit 14 through which urine flows, a sampling conduit tube 16 of known volume for retaining a sample of the urine, a disposal tube 20 for urine in excess of the sampled amount, and a combined handle and housing 18 in which the instrument's electronics are housed.

Flow leveling funnel 12 has a maximum diameter of about five inches and, with handle 18, is sized to be easily carried in a discrete package of reasonable size. The depth of funnel 12 is insufficient to permit a significant pressure head to develop, effecting the rate of acceleration of liquid out of the funnel. Outflow conduit 14 is of a known area so that the flow through the outflow conduit at a known point in the conduit is calculable.

A sampling conduit 16 and a disposal conduit 20 divide at an inverted Y in outflow conduit 14. Sampling conduit 16 includes an occluder valve 22 (shown in FIG. 2) across sampling conduit outlet 24 permitting the conduit to be closed for collecting a predetermined volume of the urine as a sample for later analysis to determine sodium concentration. The sample is released to a vial 28 after urine flow has ceased. Vial 28 is marked with the date and time to allow later comparison with the volume information. Volume information is read from a readout 26 on the face of handle 18.

Figure 2:
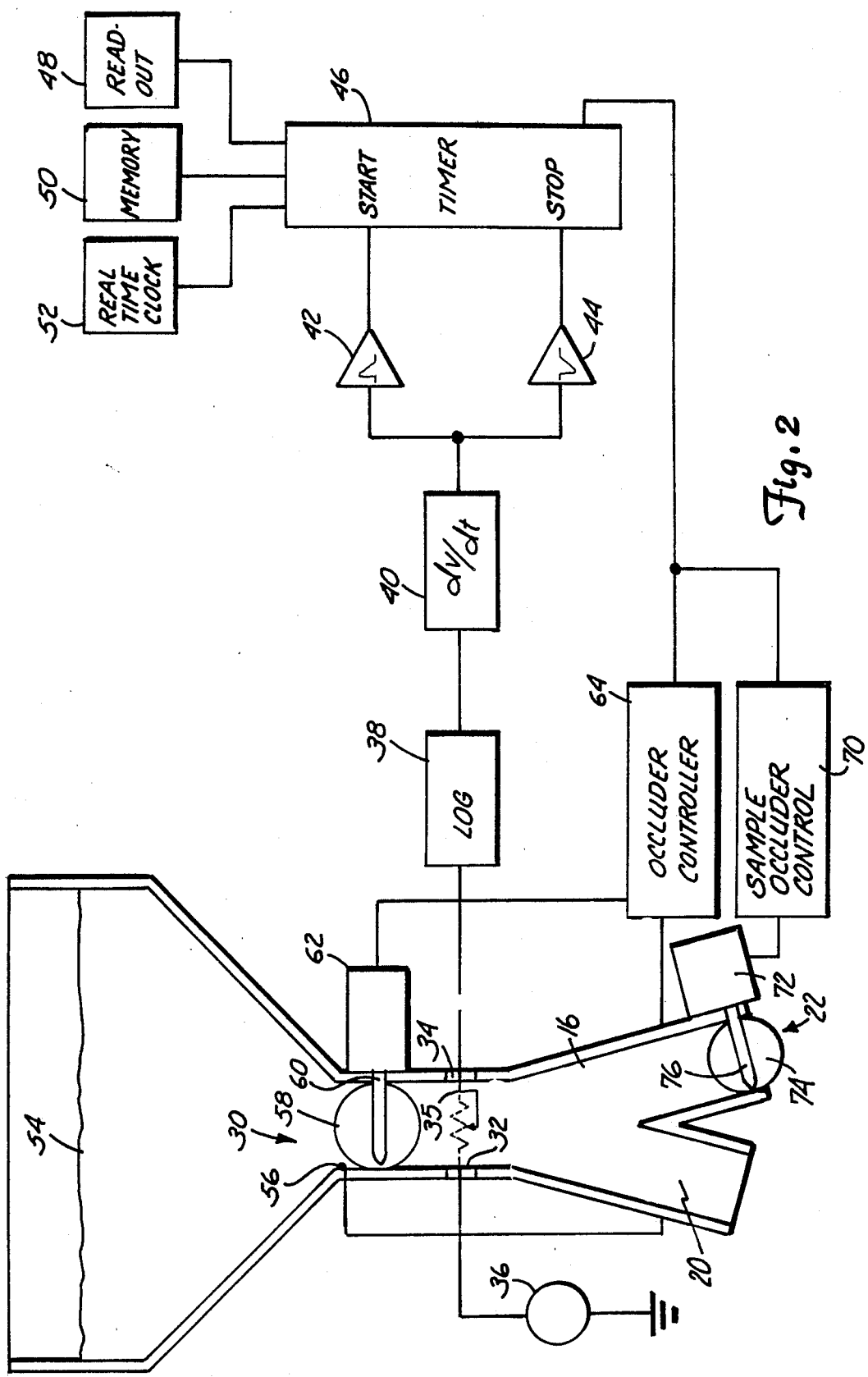
FIG. 2 is a combined block diagram of the urine volume measuring circuit and a cross sectional view of the flow rate leveling funnel and funnel outflow conduit occluding mechanism.

FIG. 2 is a block diagram circuit of the urine volume measurement apparatus and an outflow occluding mechanism 30. A pair of electrodes 32 and 34 are disposed opposite one another in outflow conduit 14. A square wave voltage source 36 is connected to electrode 32. Electrode 34 is connected to logarithmic circuit 38 which reduces the absolute voltage swings generated on electrode 34 from electrode 32. Differentiator 40 generates an output signal which is a time differential of the output from logarithmic circuit 38.

When outflow conduit 14 is dry, essentially no electrical connection is supported between electrodes 32 and 34. Introduction of urine into funnel 12 results in a stream of liquid developing in outflow conduit 14 between electrodes 32 and 34. Urine is electrically conductive and completes the circuit between electrodes 32 and 34 in much the same manner as if a variable resistor 35 had been introduced between the electrodes. Resistor 35 is shown as variable because the conductivity of urine varies from sample to sample as a function of its concentration, among other factors.

Application of an alternating potential characterized by a square waveform enhances accuracy in detecting the beginning and the cessation of urine flow in outflow conduit 14 by limiting electrolysis effects. While alternating current is commonly employed in conductivity measurements, use of a square wave enhances detection of the difference between conductivity of the urine flow and the conductivity of the consequential film of urine which develops on the inside walls of outflow conduit 14 by maintaining a signal of relatively constant magnitude with respect to ground, albeit reversing polarity, on electrode 32. Experiment has shown that the conductivity of the urine film left after cessation of urine flow through outflow conduit 14 is substantially linearly related to the conductivity of the urine in the immediately preceding flow. In general, the conductive path left by the film has about one tenth the conductivity of the preceding urine stream. Because urine varies a great deal in conductivity, it is not inconceivable that the film left by extremely concentrated urine could have been as close to the level of absolute conductivity that a stream of extremely dilute urine would have. However, the time derivative of the output of logarithm circuit 38, which indicates major changes in the resistance across outflow conduit 14 produces substantially identical magnitude pulses from differentiator 40 indicating beginning and cessation of urine flow.

Positive pulse amplifier 42 and negative pulse amplifier 44 transmit start and stop signals to timer 46. Timer 46 may be provided by a microprocessor or a table look up operation addressed to a memory, an address being provided by counting clock pulses. The timer is calibrated in milliliters which is then transmitted to a readout 48 and/or stored in memory 50 tagged for identification by a time provided by real time clock 52.

Urine flow by the individual user is continuously variable and subject to interruption. Storage in memory 50 of volume information is triggered only upon an interruption in urine flow exceeding a predetermined minimum period. The urine measuring apparatus of the present invention is adapted to compensate for low rates of urine flow to insure either a constant flow rate past electrodes 32 and 34 or no urine flow past the electrodes. Occluder mechanism 30 is disposed in funnel 12 to allow discharge of urine 54 out through outflow conduit 14 upon indiction from sensor 56 of a sufficient urine level in funnel 12. Sensor 56 is a pair of spaced electrodes adapted to detect the presence of urine at the level of the sensor through the conductivity of the urine.

Occluder mechanism 30 may be provided by any convenient technique for closing outflow conduit 14 and is shown herein as comprising a disc 58 rotatable on an axis 60 for closing the conduit in a first position and opening a conduit in a second position. Alternatively, a portion of the outflow conduit 14 may be replaced by a rubber or flexible pinch valve segment. Disc 58 is actuated by a solenoid 62 by an occluder controller 64. Occluder mechanism is opened upon indication from sensor 56 that urine is present and closed otherwise.

A cessation of urine flow for over 30 seconds is taken as indication that the void has been completed. Timer 46 is used to time breaks between urine level reaching the trip point of sensor 56. Where urine level in funnel 12 does not reach sensor 56 within 30 seconds of the closing occluder mechanism 30, upon cessation of the immediately preceding flow, completion of the void is indicated. Timer 46 will then transmit an override signal to occluder control 64 for opening occluder mechanism 30, Remaining urine in funnel 12 will be added to the total for the void. The override signal also results in sample occluder control 70 driving solenoid 72 to turn valve 22 in sampling conduit 16. Vial 28 will be detached, sealed and marked. Occluder valves 30 and 22 will remain open for three minutes allowing the user to apply appropriate cleaning agents to the device. A readout is provided on readout 48 or data transferred to memory 50. The user may then complete transfer of a sample of the void to an appropriate receptacle.

Although the present invention has been described with reference to preferred embodiments, workers skilled in the art will recognize that changes may be made in form and detail without departing from the spirit and scope of the invention.

What is claimed is:

1. A urine volume measuring apparatus for measuring urine void instance volume and collecting a urine specimen from each urine void instance in a sample receptacle, the apparatus comprising:
- a vessel for receiving and holding a changing volume of urine;
- an outflow conduit for conveying urine from the vessel at a substantially constant rate of flow;
- a sampling conduit for diverting a specimen from each urine void to a sample receptacle; and
- urine flow measuring means including isolated electrical terminals disposed in the outflow conduit, a source of alternating electrical potential connected to one of the isolated electrical terminals, a logarithmic signal generator coupled to a second one of the isolated electrical terminals, and a differentiating circuit coupled to receive signals from the logarithmic signal generator for generating opposite polarity timing signals indicating onset and cessation of urine flow through the outflow conduit;
- the urine flow measuring means being adapted to determine instances of urine flow through the outflow conduit by detection of changes in electrical conductivity between the electrical terminals and for calculating volume of the flow based on the duration of urine flow through the outflow conduit.

2. The urine volume measuring apparatus of claim 1 and further including an outflow conduit occluder positionable for blocking outflow through the outflow conduit and maintaining a minimum urine level in the vessel for maintaining a substantially constant flow rate of urine through the conduit during volume measurements.

3. The urine volume measuring apparatus of claim 2 and further comprising, a sampling conduit, a valve for trapping a known quantity of fluid from the outflow conduit in the sampling conduit and releasing the trapped quantity to a sample receptacle identifiable by the time when the urine void volume measurement was taken.

4. The urine volume measuring apparatus of claim 1 wherein the urine flow measuring means further includes a timing circuit calibrated in milliliters responsive to the opposite polarity timing signals.

5. The urine volume measuring apparatus of claim 1 wherein the urine flow measuring means further includes:
- a clock; and
- a memory for retaining data indicating urine volume and the time when urine flow was measured.

6. The urine volume measuring apparatus of claim 1 wherein the source of alternating electrical potential is a square wave generator.

7. An apparatus for measuring urine volume comprising:
- a pair of electrically isolated electrodes;
- means for collecting urine and conveying streams of urine past the isolated electrodes at a substantially constant rate of flow; and
- means for generating opposite polarity timing pulses associated, respectively, with increases and decreases in resistance between the electrodes associated with the beginning and the cessation of urine flow, including a source of alternating electrical potential connected to one of the isolated electrical terminals, a logarithmic signal generator coupled to a second one of the isolated electrical terminals, and a differentiating circuit coupled to receive signals from the logarithmic signal generator for generating the opposite polarity timing pulses indicating onset and cessation of urine flow through the outflow conduit; and
- a clock responsive to the timing pulses for determining the volume of the urine flow by timing their duration.

8. The urine volume measuring apparatus of claim 7 wherein the source of alternating potential further include a square wave generator connected to at least one of the isolated electrodes.

9. The urine volume measuring apparatus of claim 8 wherein the clock further includes a real time clock for identifying sets of urine streams by time and date of occurrence and a memory for retaining data including incidents regarding sets of urine streams.

10. A method of measuring volume quantities of an electrically conductive liquid of varying conductivity, comprising the steps of:
- applying an electrical potential to a first of pair of electrodes;
- establishing a substantially constant rate of flow of the liquid between the pair of electrodes;
- generating a logarithmic signal from the responsive potential appearing on the second electrode;
- differentiating the logarithmic signal to generate substantially equal magnitude, opposite polarity pulses associated with abrupt conductivity increases between the electrodes indicating beginning of liquid flow across the electrodes and abrupt conductivity decreases between the electrodes indicating cessation of liquid flow across the electrodes;
- timing the duration of each flow from its beginning to its cessation as indicated by the electrical pulses and the opposite polarity electrical pulses; and
- calculating the volume of the liquid from the measured duration of its flow.

11. The method of claim 10 wherein the electrical potential applied has a square waveform.

* * * * *

UNITED STATES PATENT AND TRADEMARK OFFICE
CERTIFICATE OF CORRECTION

PATENT NO. : 4,891,993
DATED : January 9, 1990
INVENTOR(S) : Kent R. Barker

It is certified that error appears in the above-identified patent and that said Letters Patent is hereby corrected as shown below:

Column 6, line 35, after "first of" insert --a--.

Signed and Sealed this

Eighteenth Day of December, 1990

Attest:

HARRY F. MANBECK, JR.

*Attesting Officer*     *Commissioner of Patents and Trademarks*